(12) United States Patent
Yuan et al.

(10) Patent No.: US 7,189,359 B2
(45) Date of Patent: Mar. 13, 2007

(54) ELECTROWETTING ELECTRODE DEVICE WITH ELECTROMAGNETIC FIELD FOR ACTUATION OF MAGNETIC-BEAD BIOCHEMICAL DETECTION SYSTEM

(75) Inventors: Shih-Jun Yuan, Taipei (TW); Jing-Tang Yang, Hsin-Chu (TW); Jer-Liang Yeh, Taichung (TW); Chih-Sheng Yu, Hsin-Chu (TW); Yi-Chiuen Hu, Hsin-Chu (TW); Chien-Jen Chen, Hsin-Chu (TW)

(73) Assignees: National Tsing Hua University, Hsin-chu (TW); Precision Instrument Development Center of National Science Council, Hsin-chu (TW)

( * ) Notice: Subject to any disclaimer, the term of this patent is extended or adjusted under 35 U.S.C. 154(b) by 50 days.

(21) Appl. No.: 10/900,649

(22) Filed: Jul. 28, 2004

(65) Prior Publication Data

US 2005/0056569 A1  Mar. 17, 2005

(30) Foreign Application Priority Data

Jul. 29, 2003  (TW)  ............................. 92120724 A

(51) Int. Cl.
*G01N 15/06* (2006.01)
*B32B 5/02* (2006.01)
*B32B 27/04* (2006.01)
*B32B 27/12* (2006.01)
*B32B 27/00* (2006.01)

(52) U.S. Cl. ....................... 422/82.01; 422/50; 422/55; 422/68.1; 422/82.02; 436/43; 436/149; 436/63

(58) Field of Classification Search ................. 422/50, 422/55, 68.1, 82.01, 82.02; 436/43, 149, 436/63; 29/592, 592.1
See application file for complete search history.

(56) References Cited

U.S. PATENT DOCUMENTS

| | | | |
|---|---|---|---|
| 5,655,665 A | | 8/1997 | Allen et al. |
| 5,945,898 A | * | 8/1999 | Judy et al. .................... 335/78 |
| 6,342,396 B1 | * | 1/2002 | Perrin et al. ................ 436/518 |
| 6,565,727 B1 | | 5/2003 | Shenderov |
| 6,623,984 B1 | * | 9/2003 | Fleischman et al. ......... 436/526 |
| 6,806,050 B2 | * | 10/2004 | Zhou et al. .................... 435/6 |
| 6,858,184 B2 | * | 2/2005 | Pelrine et al. ............. 422/68.1 |

* cited by examiner

*Primary Examiner*—Brian Sines
(74) *Attorney, Agent, or Firm*—Alston & Bird LLP

(57) ABSTRACT

A detecting device for biochemical detections is provided. The detecting device includes a first substrate, a magnetic layer located on the first substrate, an isolation layer located on the magnetic layer, at least a first electrode located on the isolation layer, a first dielectric layer located on the first electrode, a first hydrophobic layer located on the first dielectric layer, a second substrate, at least a second electrode located on the second substrate and having a cathode and an anode, a second dielectric layer located on the second electrode' and a second hydrophobic layer located on the second dielectric layer. The first electrode is zigzag-shaped, and the cathode and the anode of the second electrode are comb-shaped and interlaced with each other.

10 Claims, 18 Drawing Sheets

US 7,189,359 B2

ELECTROWETTING ELECTRODE DEVICE WITH ELECTROMAGNETIC FIELD FOR ACTUATION OF MAGNETIC-BEAD BIOCHEMICAL DETECTION SYSTEM

FIELD OF THE INVENTION

The present invention is related to a magnetic-bead biochemical detecting device, in particular, to a magnetic-bead biochemical detecting device controlled by an electromagnetic field, which is induced by an electrowetting actuated electrode.

BACKGROUND OF THE INVENTION

The separation is the critical technique involved in the biochemical detecting. Separation techniques, such as the physical filtration, crystallization and distillation have been widely applied to separate cells or fragments of cells from aqueous solutions or suspensions However, these techniques have become more and more insufficient as the quantity of the material to be purified becomes smaller and the compactness of the detecting device needs to be realized.

The magnetic separation is a well-known technique in the biotechnology, and the magnetic beads have recently been used to help the manipulating and transporting of bio-molecules. It is possible to satisfy the above demands by adopting the magnetic-bead separation technique for the flexibility in controlling.

The working principle of the magnetic-beads separation technique is that the target cells and bio-molecules would be separated form the sample liquid and then transmitted to a specific position by the magnetic-beads via the sampled cells or bio-molecules adsorbed on the magnetic beads. Many efforts have been done in this technique. Not only the microfluidic channels, the micromechatronics processing and the electromagnet, which is used for attracting and adsorbing the magnetic beads, but also the shapes, the sizes and the fabrications of the electromagnets have been developed already. Furthermore, the applications for the biochemical detectings including the relevant biochemical reactions, the detecting processes and the signal measurements also have been mentioned.

Please refer to FIGS. 1, 2 and 3, wherein FIG. 1 is a schematic view illustrating the structure of a first conventional magnetic-bead biochemical detecting device 1', FIG. 2 is a cross-sectional view according to the line A–A' in FIG. 1, and FIG. 3 illustrates the structure of the electromagnet of the detecting device 1' in FIG. 1. As shown in FIGS. 1 and 2, the detecting device 1' is mainly formed by a substrate 18', an electromagnet 13' located thereon having an embedded serpentine conductor structure 23', the magnetic layer 24' of a permalloy and a microfluidic channel 12' with a gap layer 16' therebetween. Furthermore, bonding pods 17' are configured to make an electric connection to the electrically driving system (not shown), and a fluid inlet 11' and a fluid outlet 14' are configured on a lid 15', which may be made of glasses. The embedded serpentine conductor structure 23' of the electromagnet 13' has plural conducting wires 34', one of which is further enlarged in FIG. 3.

Accordingly, the electromagnet 13' is an additional arrangement to the microfluidic channel 12', wherein the electromagnet 13' and the microfluidic channel 12' are independently fabricated on different chips and then joined together. The electromagnet 13' itself could not drive the fluid to flow, and an additional fluid driver is hence needed. The fluid driver makes the detecting process more complicated and a less precise detection result would be resulted therefrom. Therefore, such a detecting device 1' is used only for magnetic-beads detecting and lacks the applicability and the benefit in integration.

Besides, since the detecting device 1' mentioned above is configured to be operated through the continuous flow, it has a lot of drawbacks, such as a large amount of the reagent is necessary, the samples mixing is insufficient, it is much difficult to drive the fluids, the problem of time-consuming is serious and the detecting result is not precise enough.

Please refer to FIG. 4 illustrating the structure of a second detecting device according to the prior art. The detecting device 4' disclosed in the U.S. Pat. No. 6,116,863 includes plural electromagnetic drivers 41' disposed on a first substrate 40' and a spiral coil 42' encapsulated by an overlapping magnetically permeable core 43'. Furthermore, a second substrate 50' is also used in the detecting device 4' to form a diaphragm 48'and a boss 46', and a magnetic permeable material 45' may be electroplated on the diaphragm 48'. Additionally, a third substrate 60' is applied to form valve seats 47' and a microfluidic channel 49'. Such a detecting device 4' is further improved to apply in the magnetic controlling and detecting.

Please refer to FIG. 5, which schematically illustrates the electromagnetic driver 41' in FIG. 4 in greater detail. The spiral coil 42' includes an outer lead wire 42a' and an inner lead wire 42b'. An insulator layer (not shown) interposed between the out lead wire 42a' and the inner lead wire 42b' generally insulates the spiral coil 42' from the core 43'. Furthermore, the electromagnetic driver 41' has a central via 51' and a plurality of peripheral vias 52'.

Please refer to FIG. 6 illustrating a magnetic particle separator 6' according to the prior art. The magnetic particle separator 6' disclosed by the U.S. Pat. No. 5,655,665 includes a microfluidic channel 63' and two integrated inductive components 61' respectively located on one side of the microfluidic channel 63'. The integrated inductive components 61' are configured to attract and adsorb the magnetic beads thereon. The ends 62' of the magnetic cores of the inductive components 61' are disposed adjacent to the microfluidic channel 63' and the conductors of the inductive components 61' are electrically coupled to bonding pads 64' which, in operation, receive a DC voltage. Please refer to FIG. 7, which is an enlarged schematic diagram illustrating the structure of the integrated inductive component 61' in FIG. 6. Accordingly, the integrated inductive component 61' is realized by wrapping the magnetic core 71' around a planar meander conducting line 72'. In such a designed magnetic particle separator, however, the continuous flow is utilized for the magnetic-beads operating and controlling, and an additional driver (not shown) for driving the fluid to flow is still needed.

The above descriptions demonstrate the technical principles and applications of the magnetic-beads detecting technique. Moreover, the technique relative to electrowetting will be further explained as follows.

The electrowetting relates to the phenomenon that the hydrophobic-hydrophilic conversion of the droplets is occurred between the droplet and the contact surface, and the conversion would be affected by an applied electric potential. The droplet is further being driven to move by the surface tension imbalance thereof. Methods of adopting the phenomenon for driving the fluid are almost completely developed. Accordingly, several fundamental operations for droplets, in particular, the fluid mixing based on the droplets, could be operated by a single arrangement. The droplets are able to move in a plane of two-dimension through a specific arrangement of the electrode, which improves the degree of freedom and the practicability of the electrowetting actuated device.

Please refer to FIG. 8, which illustrates the conventional electrowetting actuated device. The electrowetting actuated device 8' is mainly configured by an electrode 84' on a substrate 82', and a gap 83' is formed therebewteen. Moreover, the electrowetting actuated device 8' has a lid 81' covered thereon for protection. It is worthy to be mentioned that the electrode 84' in the electrowetting actuated device 8' is just designed to drive the droplets 85' through the disclosed shape of the electrode 84', which has limited the practicability of the electrowetting actuated device 8'.

Therefore, it is predictable that the electrowetting actuated device will have an additional function by changing the shapes and arrangements of the electrodes and its practicability will be improved accordingly, while the droplets are driven to move.

Please refer to FIG. 9 illustrating the electrode set, which is disclosed by the prior art, U.S. Pat. No. 6,565,727. The electrode set 9' includes a plurality of electrodes 91' and a circular arrangement of sectorial electrodes 92'. Such an electrode set enables the fluid to move in circular.

As a result, it is apparent that a specific function of the electrowetting actuated device would be achieved by a specific arrangement or a specific shape of the designed electrodes. However, an integrated function of the magnetic-beads detecting technique with the electrowetting driving technique is not realized nowadays.

In order to overcome the drawbacks in the prior art, it is feasible to replace the continuous flows by the droplets in the magnetic-beads detecting technique. In other words, it is a more potential application of combining the electrowetting device with the magnetic-beads detecting device through a novel arrangement of the electrode.

Based on the above, it is possible to provide a more complete, convenient and practical detecting system by combining the electrowetting actuated device with the magnetic-beads detecting device, in particular, by integrating the electromagnet of the detecting device with the electrode of the electrowetting actuated device. The integrated detecting device provided by the present invention is fabricated through a simpler process, and can improve the efficiency of the conventional magnetic-beads biochemical detecting system.

SUMMARY OF THE INVENTION

In accordance with the main aspect of the present invention, a detecting device for magnetic-beads detecting is provided. The detecting device actuated by the electric field induced by an electrowetting electrode includes a first substrate, a magnetic layer located on the first substrate, an isolation layer located on the magnetic layer, at least a first electrode located on the isolation layer, a first dielectric layer located on the first electrode, a first hydrophobic layer located on the first dielectric layer, a second substrate, at least a second electrode located on the second substrate and having a cathode and an anode, a second dielectric layer located on the second electrode, and a second hydrophobic layer located on the second dielectric layer.

Preferably, the first electrode is zigzag-shaped.

Preferably, the cathode and the anode are comb-shaped and are interlaced with each other.

Preferably, the detecting device is a magnetic-bead biochemical detecting device for detecting a target in a plurality of magnetic beads of a droplet.

Preferably, the first substrate and the second substrate are respectively configured to make the first electrode and the second electrode face to each other and to form a gap therebetween.

Preferably, the droplet is movable in the gap by a voltage difference produced between the first electrode and the second electrode, and a magnetic force for attracting the plurality of magnetic beads is induced by applying currents only on the first electrode.

Preferably, a positive-and-negative interlaced electric field is generated by applying currents on the cathode and the anode for initiating a certain reaction of the target to further generate a signal of current to be detected.

Preferably, the magnetic layer is magnetized by the magnetic force.

Preferably, a plurality of magnetic lines of force is closed by the magnetic layer so as to reduce a dissipation of the plurality of magnetic lines of force and to enhance the magnetic force.

Preferably, the reaction is an oxidation-reduction reaction.

Preferably, the first substrate is a silicon substrate.

Preferably, the first electrode is made of a metal.

Preferably, the magnetic layer is made of a permalloy.

Preferably, the second substrate is a glass substrate.

Preferably, the second electrode is made of a transparent and electrically conductive material.

Preferably, the signal of current is forwarded by the cathode and the anode for being detected.

In accordance with another aspect of the present invention, a detecting device for magnetic-beads detecting is provided, wherein the detecting device is actuated by the electric field induced by an electrowetting electrode. The detecting device includes a first substrate, at least a first electrode located on the first substrate, a second substrate, and at least a second electrode located on the second substrate and having a cathode and an anode.

Preferably, the first electrode is zigzag-shaped.

Preferably, the cathode and the anode are comb-shaped and are interlaced with each other.

Preferably, the detecting device further includes a first dielectric layer and a first hydrophobic layer in turn on the first electrode.

Preferably, the detecting device further includes an isolation layer and a magnetic layer in turn between the first electrode and the first substrate.

Preferably, the magnetic layer is made of a permalloy.

Preferably, the first substrate and the second substrate are respectively configured to make the first electrode and the second electrode face to each other and to form a gap therebetween.

Preferably, the droplet is movable in the gap by a voltage difference produced between the first electrode and the second electrode.

Preferably, a magnetic force for attracting the plurality of magnetic beads is induced by applying currents only on the first electrode, and a positive-and-negative interlaced electric field is generated by applying currents on the cathode and anode for initiating a certain reaction of the target to further generate a signal of current to be detected.

Preferably, the magnetic layer is magnetized by the magnetic force.

Preferably, a plurality of magnetic lines of force of the magnetic force is closed by the magnetic layer so as to reduce a dissipation of the magnetic line of force and to enhance the magnetic force.

In accordance with another aspect of the present invention, a detecting device used for magnetic-beads detecting and actuated by the electric field induced by an electrowetting electrode is provided. The detecting device includes a first substrate, at least a first electrode located on the first substrate, a second substrate, and at least a second electrode located on the second substrate and having a cathode and an anode.

Preferably, the cathode and the anode are comb-shaped and are interlaced with each other.

The foregoing and other features and advantages of the present invention will be more clearly understood through the following descriptions with reference to the drawings, wherein:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
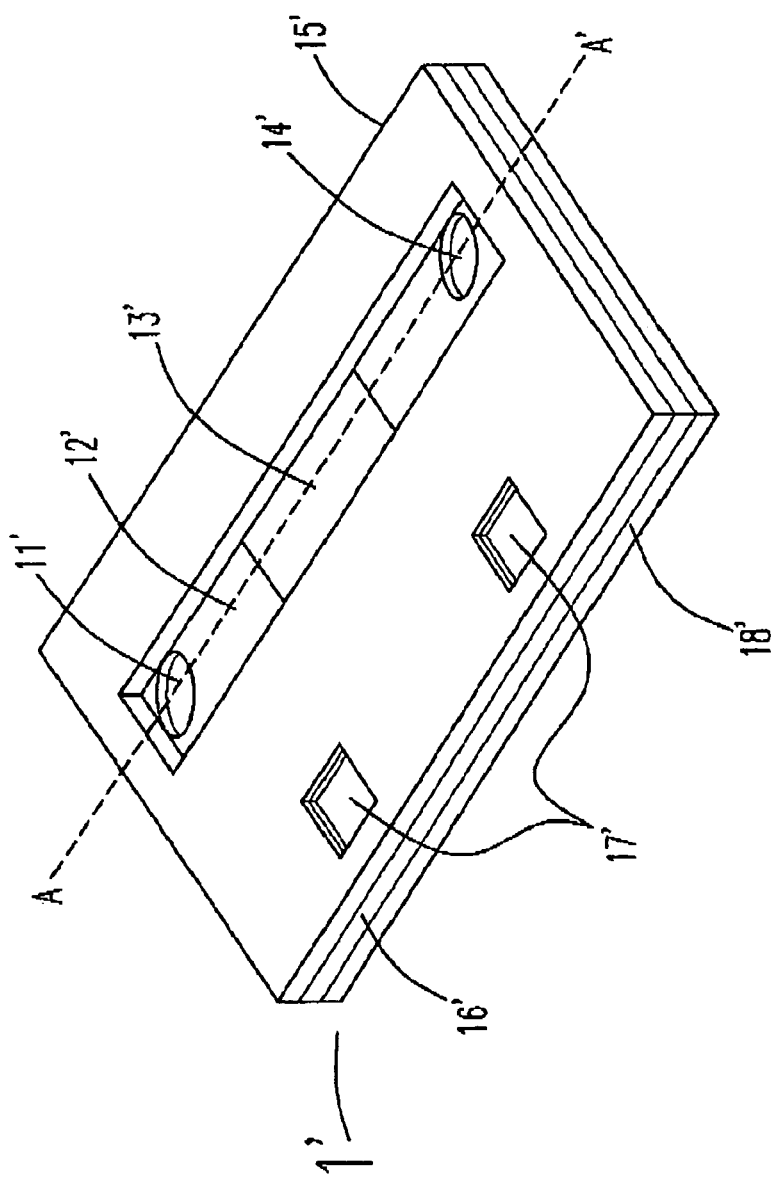
FIG. 1 is a schematic view illustrating the structure of a first magnetic-beads biochemical detecting device according to the prior art.
Figure 2:
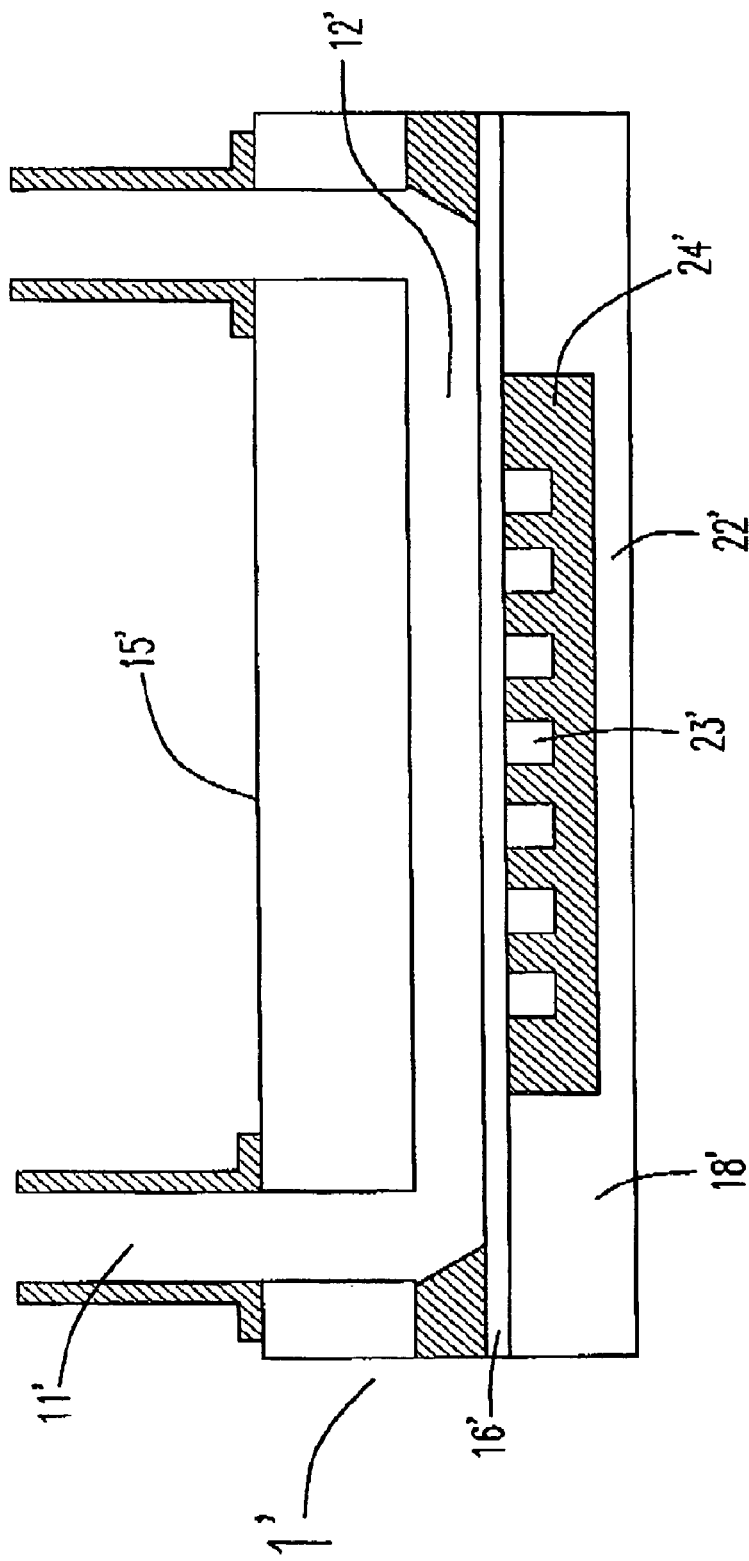
FIG. 2 is a cross-sectional view according to the line A–A' in FIG. 1.
Figure 3:
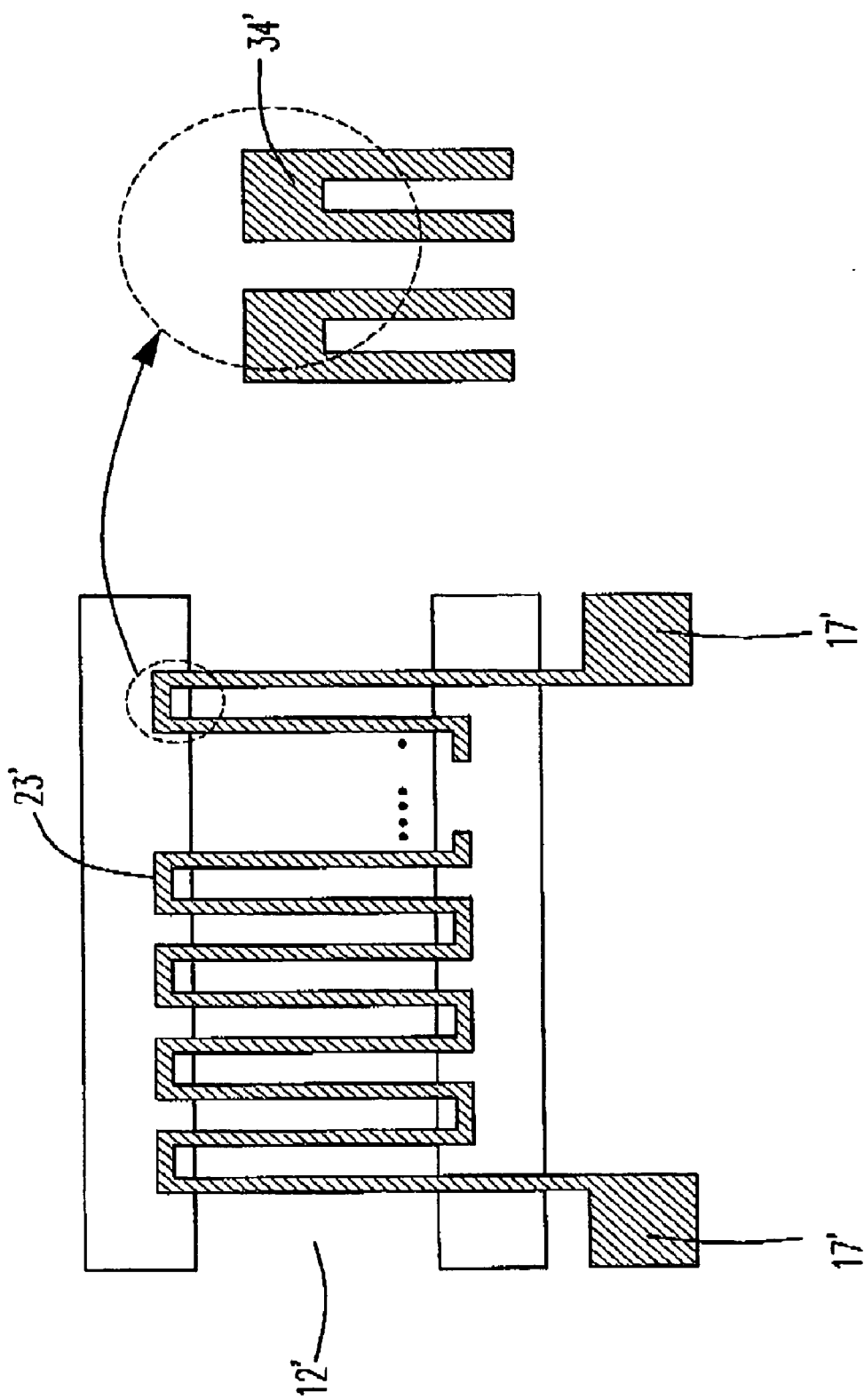
FIG. 3 is a diagram illustrating the structure of the electromagnet of the first magnetic-beads biochemical detecting device according to the prior art.
Figure 4:
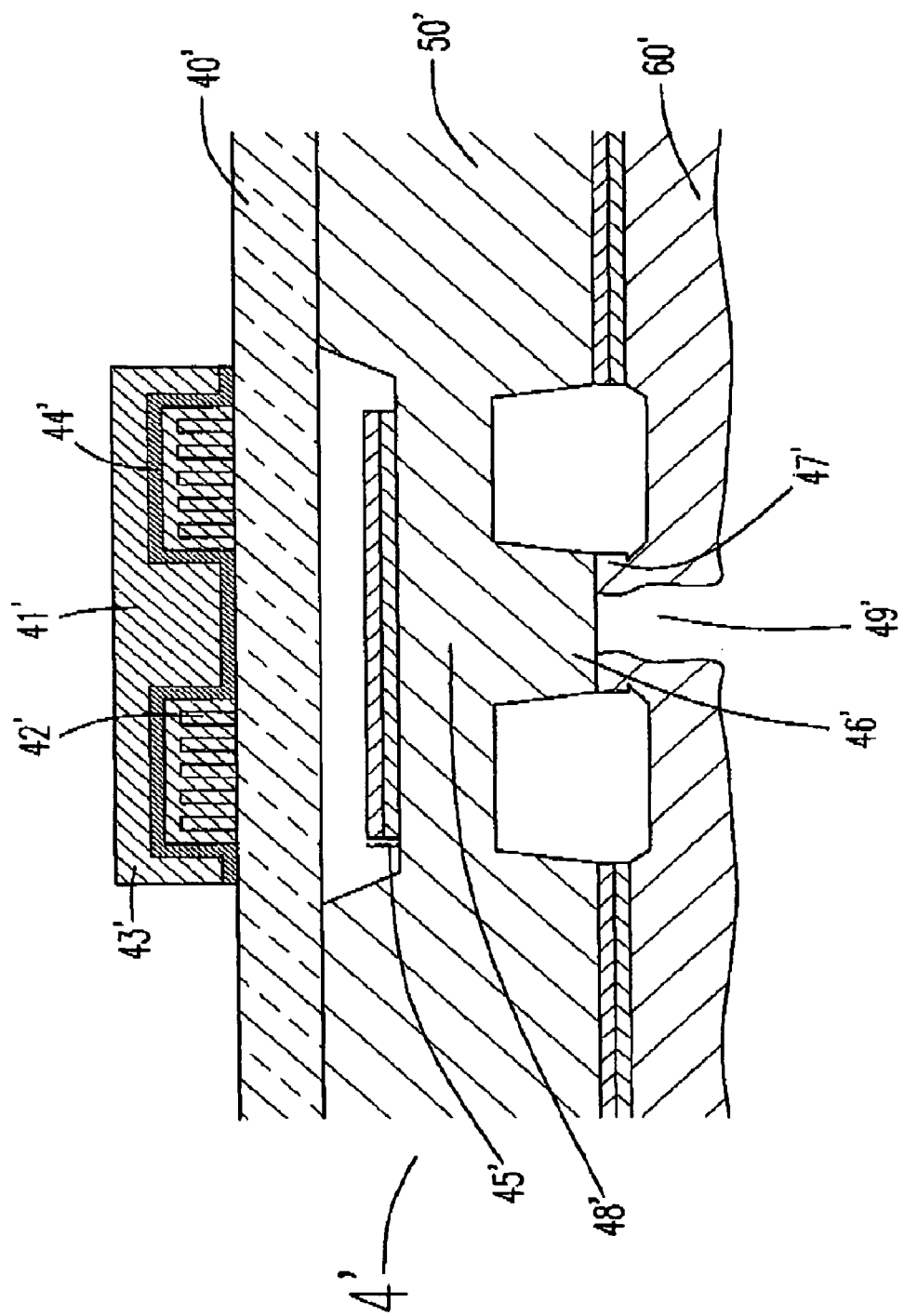
FIG. 4 is a diagram illustrating the structure of a second magnetic-beads biochemical detecting device according to the prior art.
Figure 5:
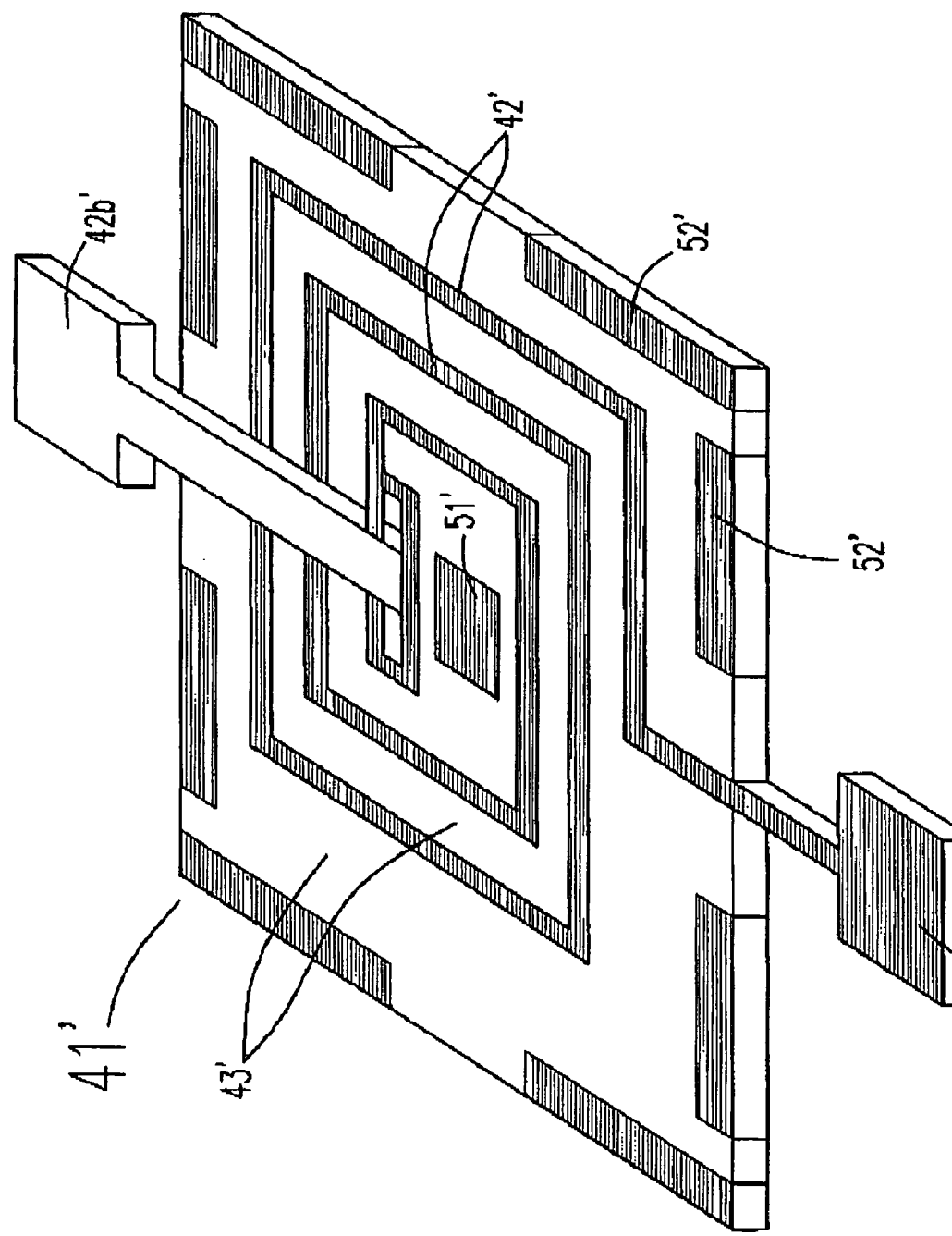
FIG. 5 is a diagram schematically illustrating the electromagnetic driver of the detecting device in greater detail according to FIG. 4.
Figure 6:
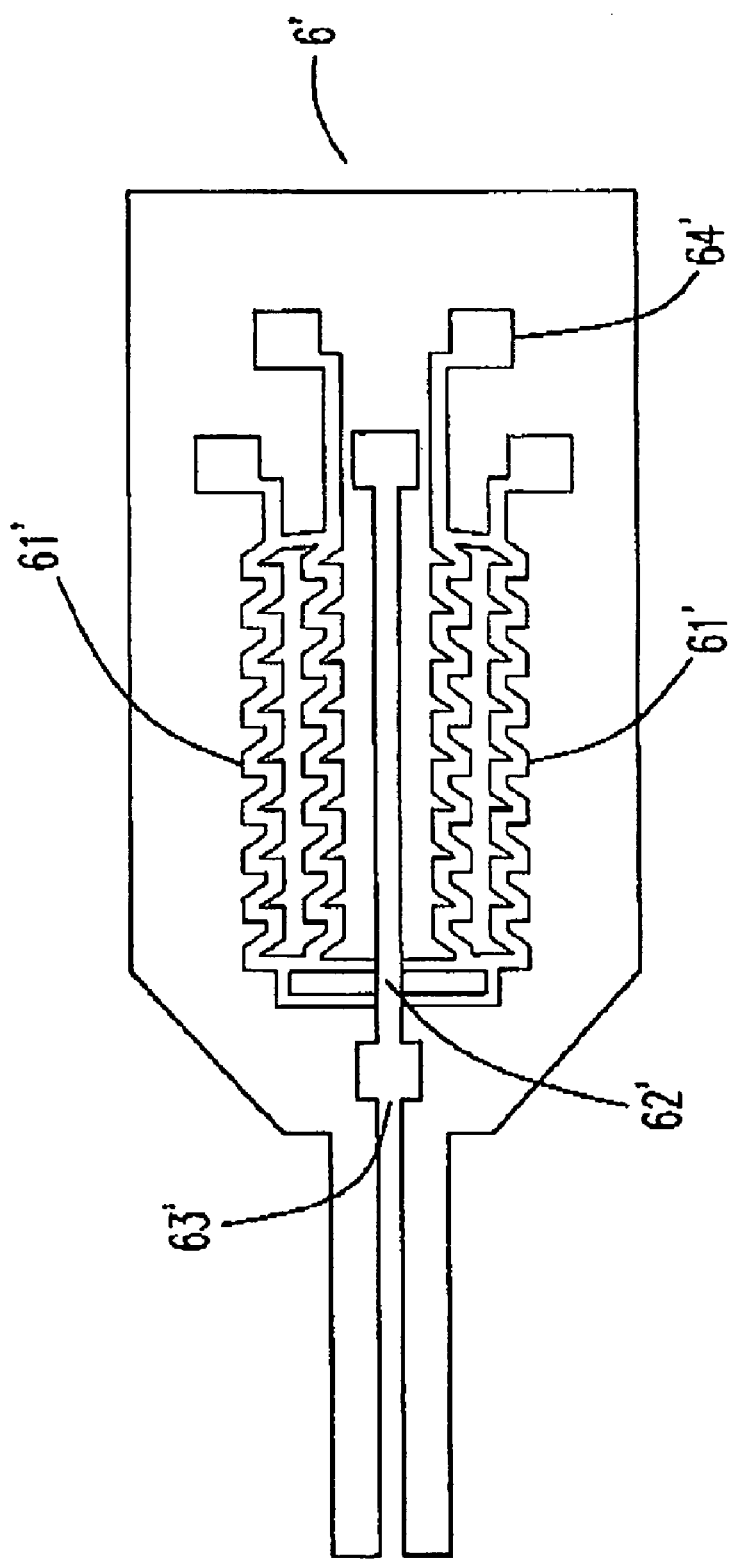
FIG. 6 is a diagram illustrating a magnetic particle separator according to the prior art.
Figure 7:
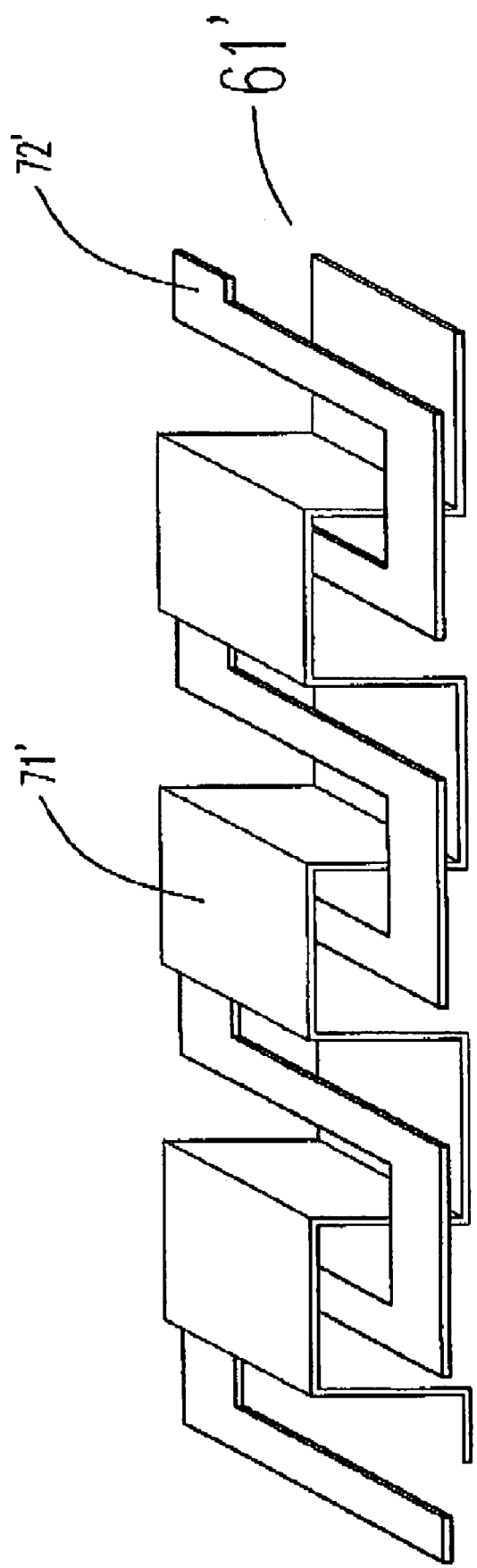
FIG. 7 is an enlarged schematic diagram illustrating the structure of the integrated inductive component of the magnetic particle separator according to FIG. 6.
Figure 8:
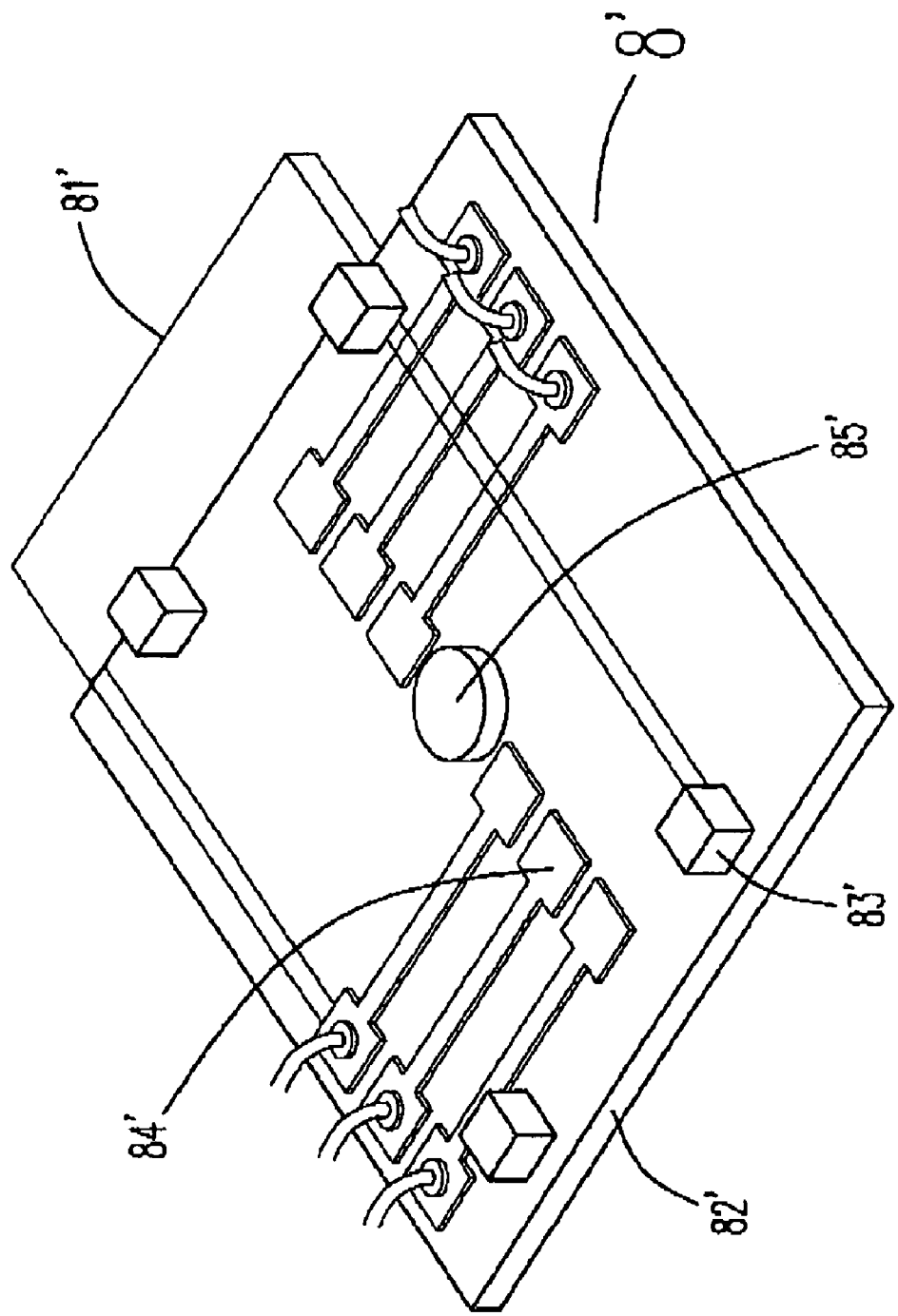
FIG. 8 is a diagram illustrating the conventional electrowetting actuated device according to the prior art.
Figure 9:
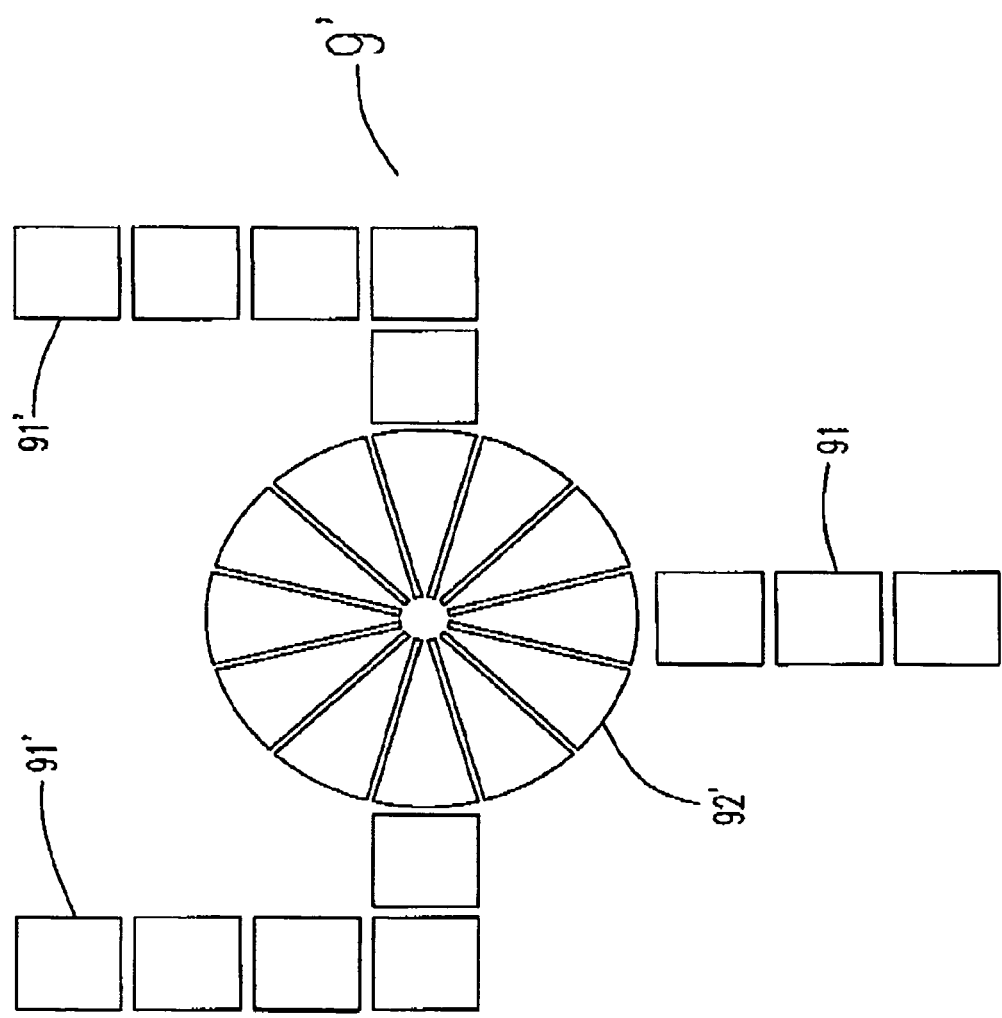
FIG. 9 is a diagram illustrating the electrode arrangement of the electrowetting actuated device according to the prior art.
Figure 10A:
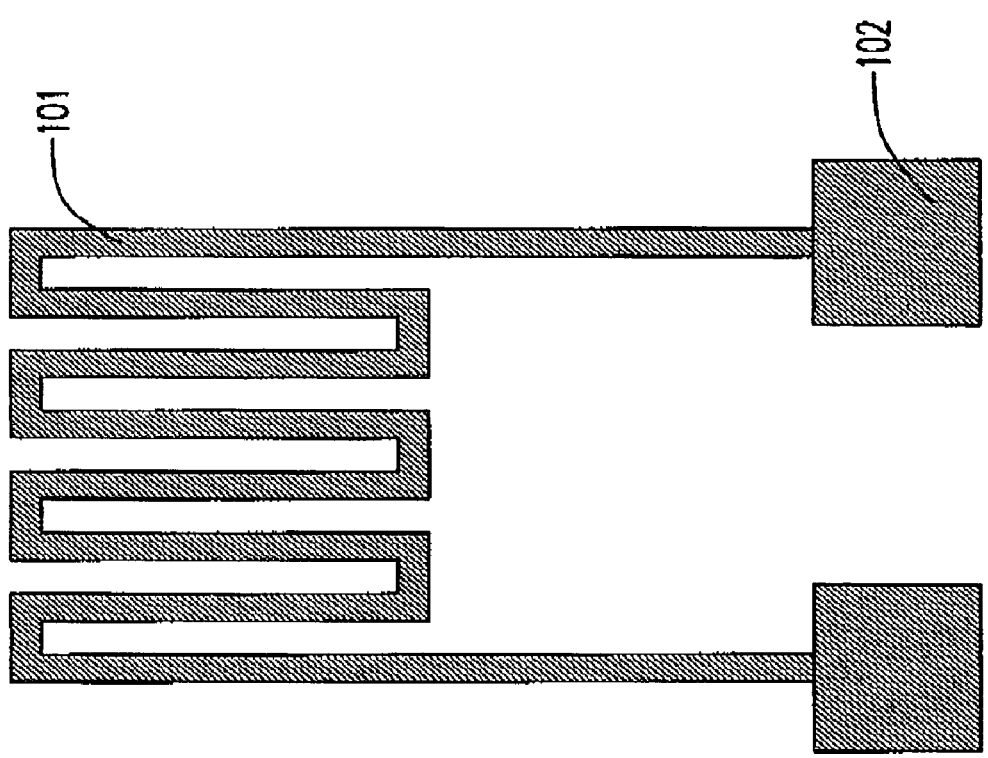
FIGS. 10(a) to 10(c) are diagrams illustrating the shapes and arrangements of the electrodes according to a preferred embodiment of the present invention.
Figure 10B:
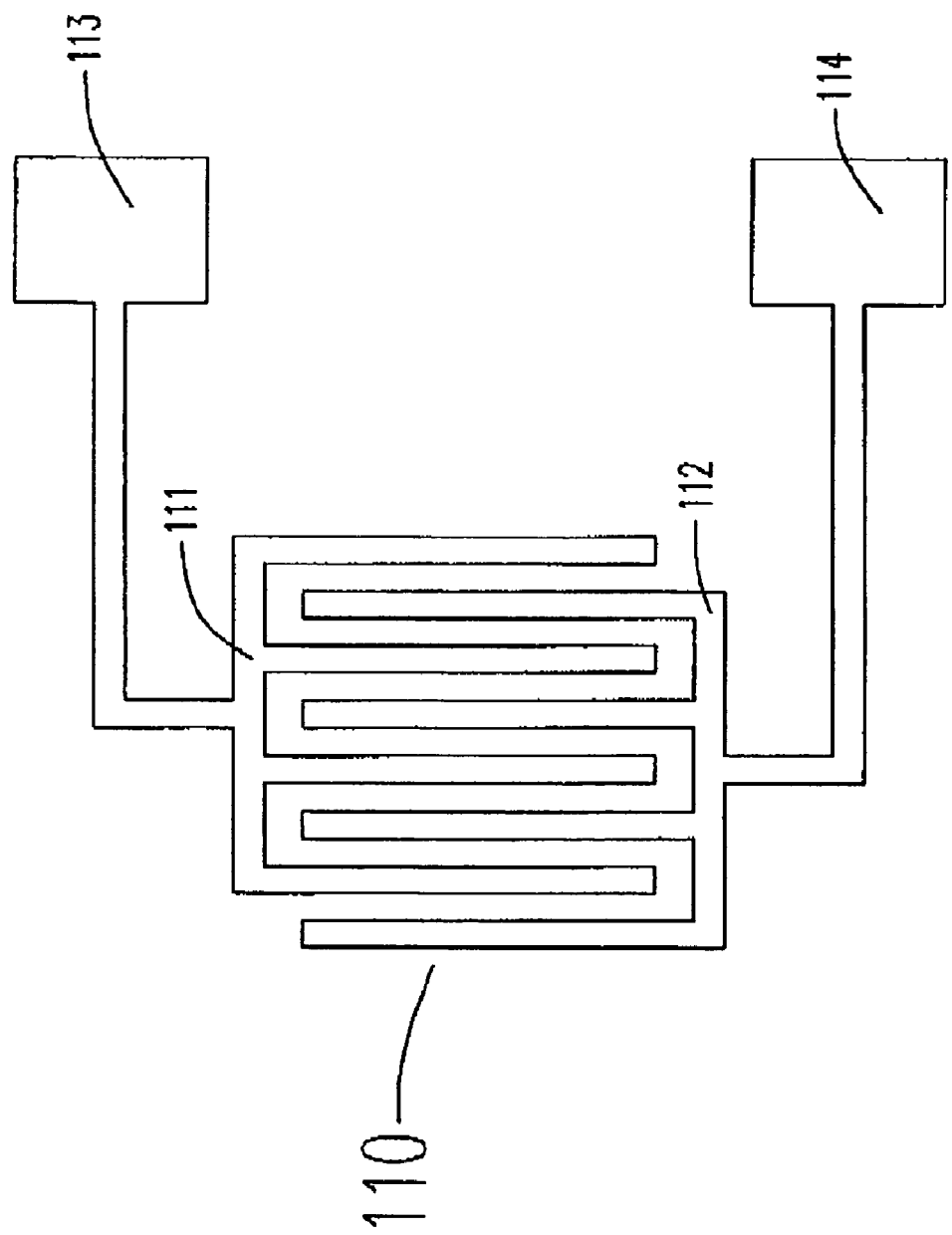
Figure 10C:
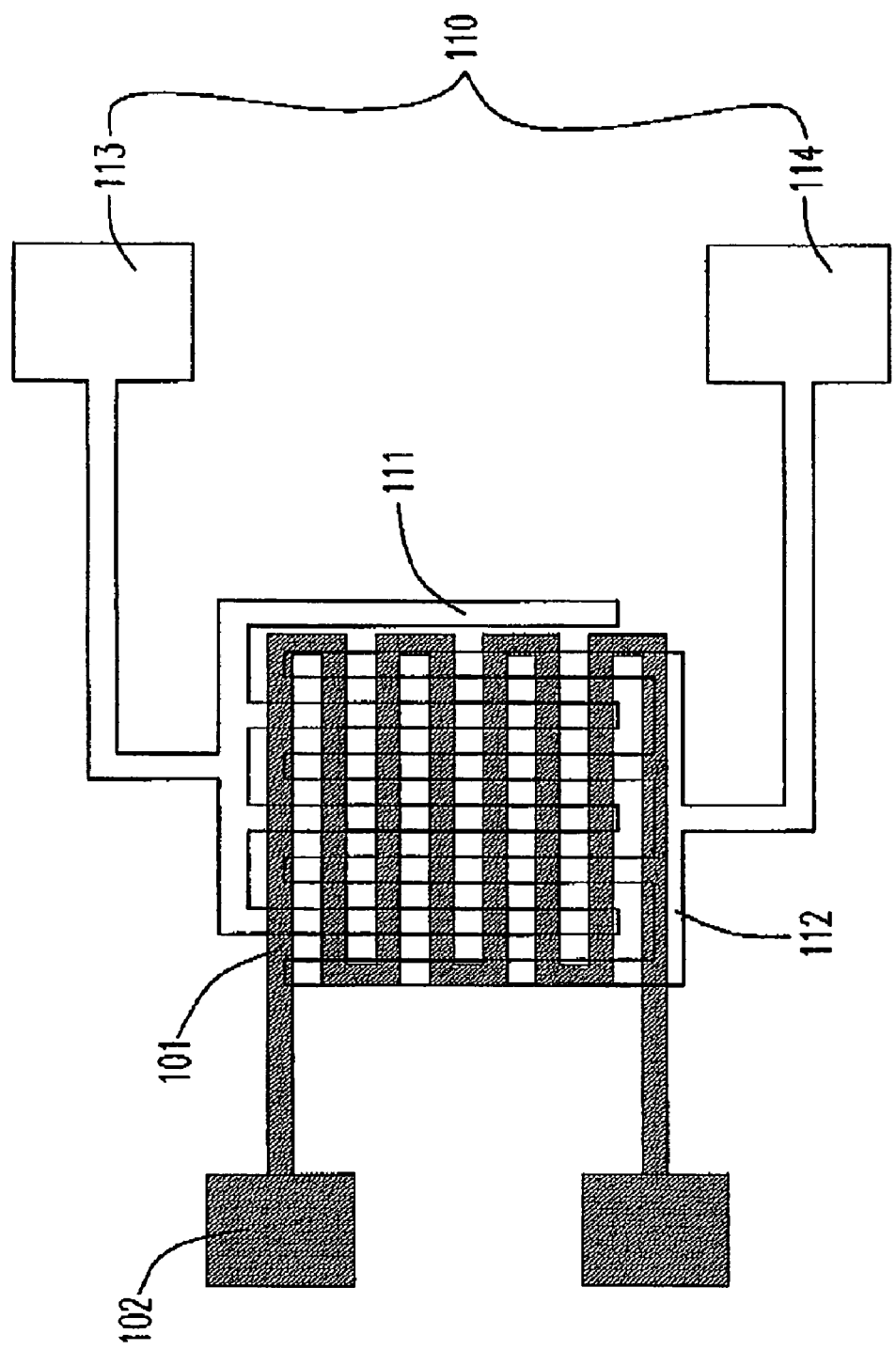

Please refer to FIGS. 10(a) and 10(b), which respectively illustrate the shapes of the first and the second electrode according to a preferred embodiment of the present invention. A first electrode 101 is designed as zigzag-shaped and has two ends of bonding pods 102, as shown in FIG. 10(a). As shown in FIG. 10(b), a second electrode 110 having a first sub-electrode 111 and a second sub-electrode 112, which are comb-shaped and interlaced with each other, and respectively have ends of binding pods 113 and 114. Accordingly, FIG. 10(c) shows the assembly association of the first electrode 101 and the second electrode 110.

Figure 11:
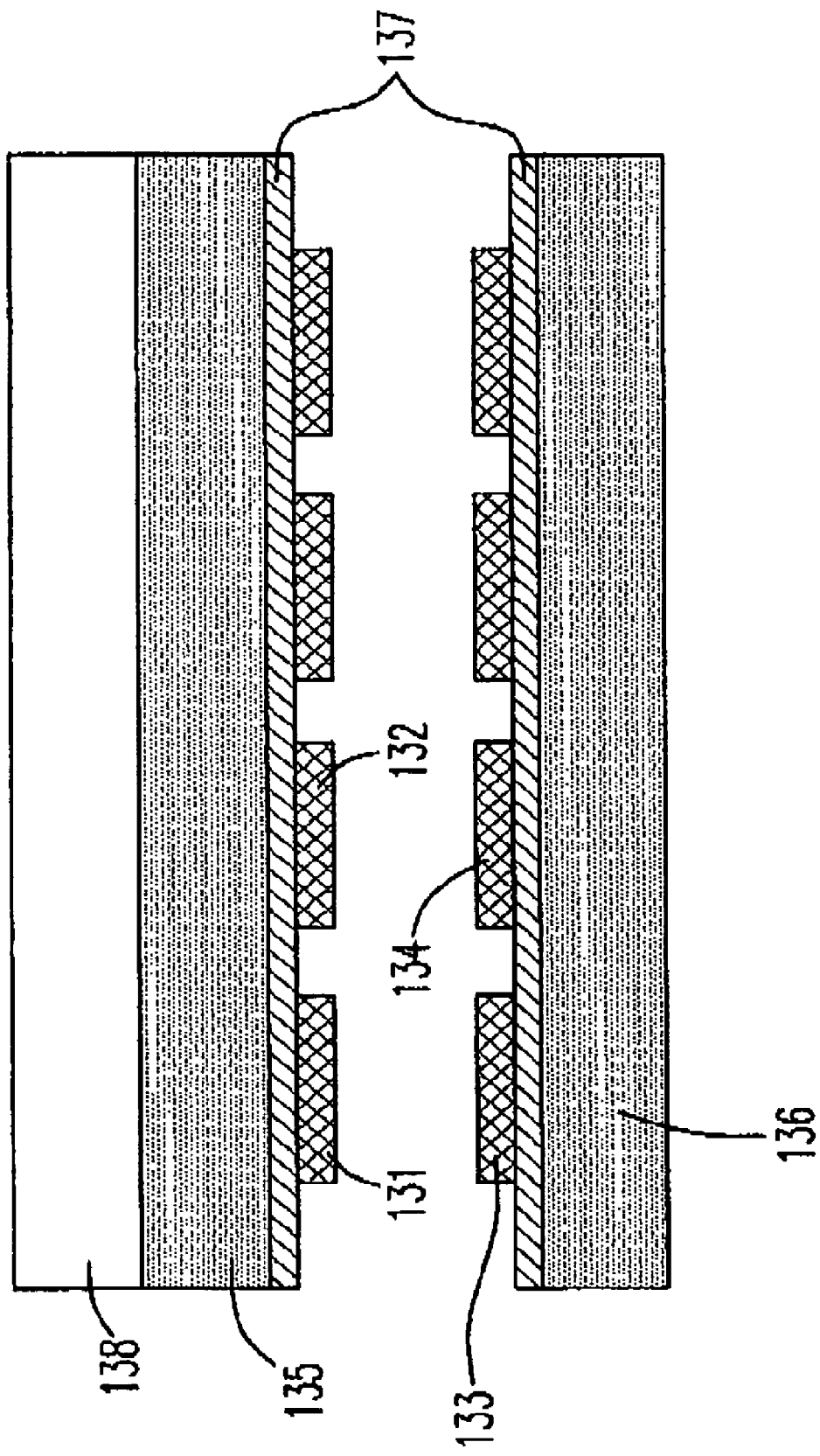
FIG. 11(a) is a side view illustrating the detecting device according to the preferred embodiment of the present invention.
FIG. 11(b) is a top view illustrating the electrode arrangement in the detecting device according to the preferred embodiment of the present invention.
Figure 11:
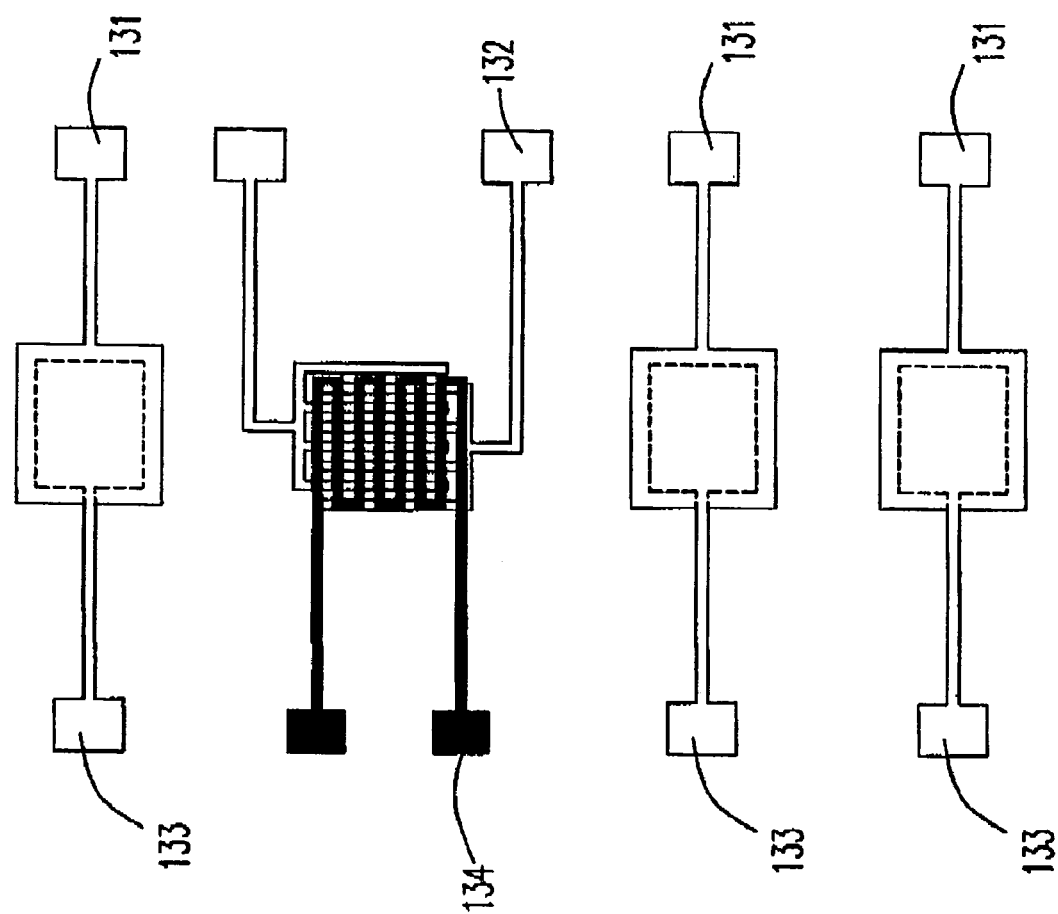

Please refer to FIG. 11(a) and FIG. 11(b), wherein FIG. 11(a) is a side view illustrating the detecting device of the present invention, and FIG. 11(b) is a top view of the electrode arrangements accordingly. A dielectric and hydrophobic layer 137 is respectively deposited on a first substrate 135 and a second substrate 136, which are faced to each other. The upper electrode 131 and the lower electrode 133 are respectively formed on the dielectric and hydrophobic layer 137, and a lid 135 is covered thereon for protection. By the function of the comb-shaped second electrode 132 and the zigzag-shaped first electrode 134 of the present invention, the detecting device would be operated not only for magnetic-beads detecting, but also for droplets driving.

Figure 12:
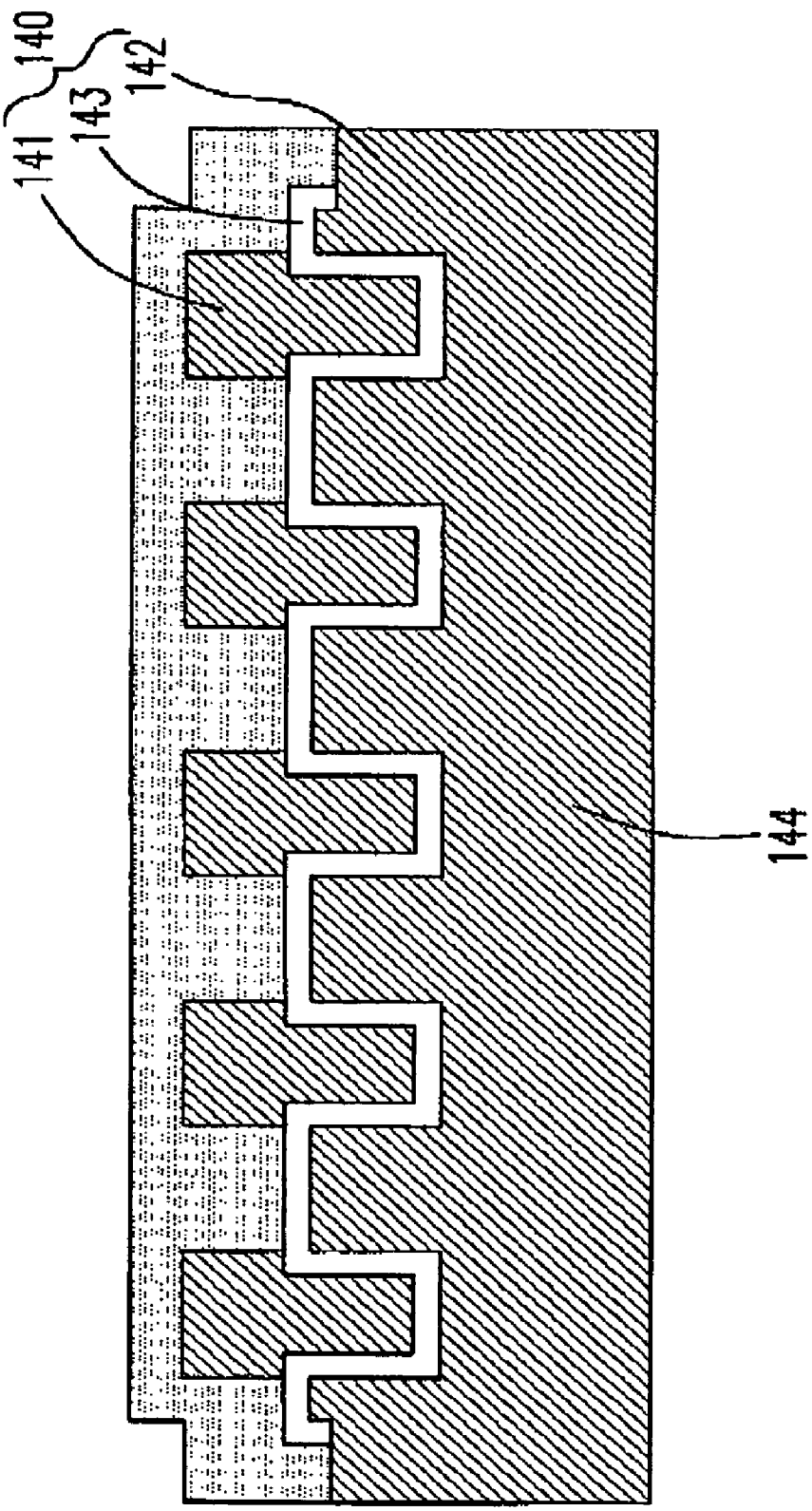
FIG. 12 is a side view illustrating the electromagnet in the detecting device according to the preferred embodiment of the present invention.

Please refer to FIG. 12. The electromagnet of the detecting device according to the present invention is provided by an embedded serpentine conductor structure with a semi-encapsulated planar electromagnet on a substrate. A magnetic field is induced by applying a current to the electromagnet 140 on a substrate 144. The electromagnet 140 is formed by a zigzag-shaped electrode 141, a permalloy core 142 and an isolation layer 143 therebetween. The magnetic beads are attracted through the induced magnetic field and the permalloy core 142 is also magnetized by the induced magnetic field. Besides, the permalloy core 142 would make the magnetic lines of force closed, and reduce the dissipation of the magnetic lines of force to further enhance the induced magnetic field. The electromagnet 140 provided in the present invention is multiplex and is able to be used for driving the droplets to move. Additionally, a complicated process for manufacturing and assembling the electrodes is not necessary in the present invention.

Figure 13:
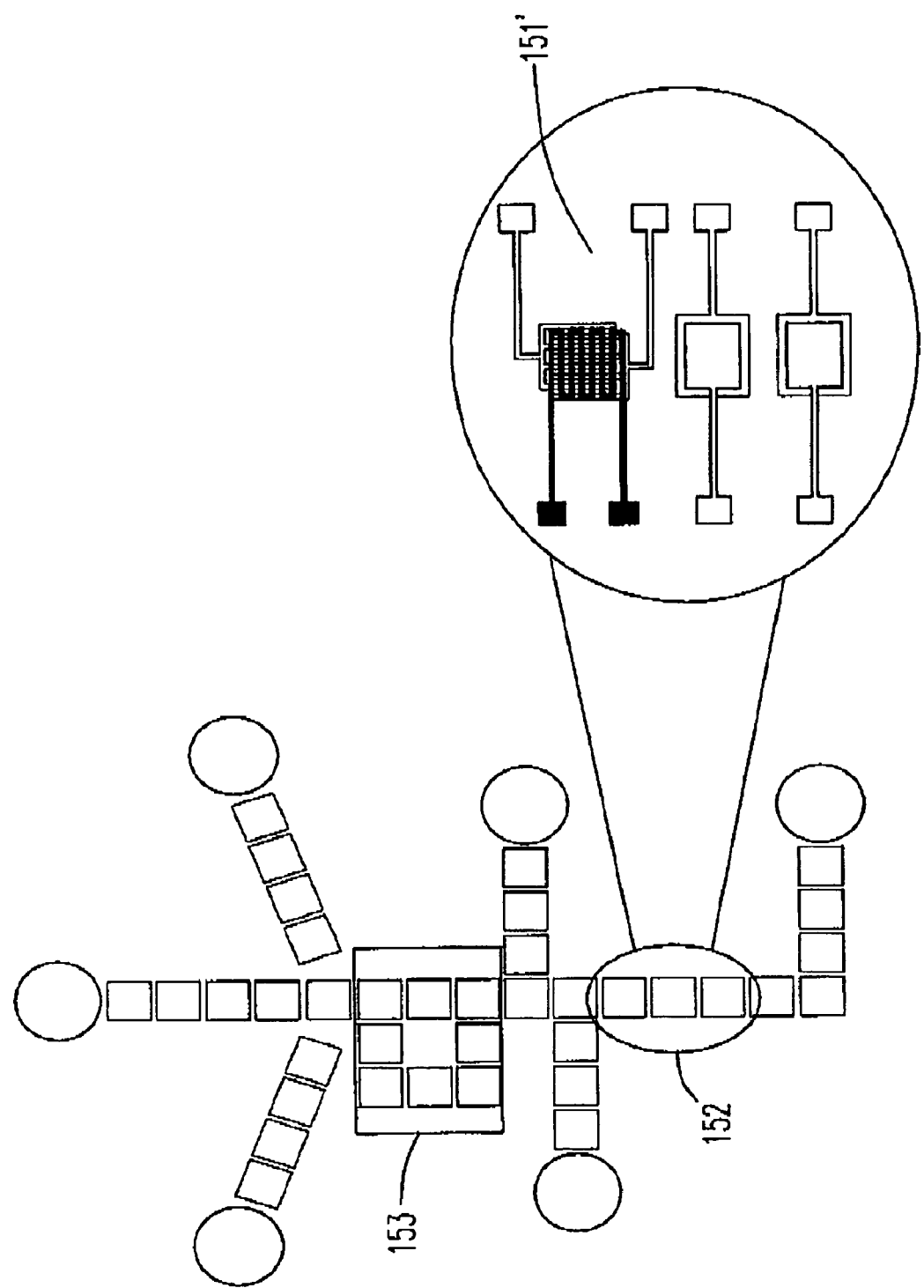
FIG. 13 is a diagram illustrating the application of the electrode in the detecting device according to the preferred embodiment of the present invention.

Please refer to FIG. 13 illustrating the application of the electrodes, which are arranged according to the present invention. The electrode set 151 having a zigzag-shaped electrode and a comb-shaped electrode both provided by the present invention, is applied in a detecting zone 152 for detection and in a mixing zone 153 for completely mixing the fluids.

Figure 14A:
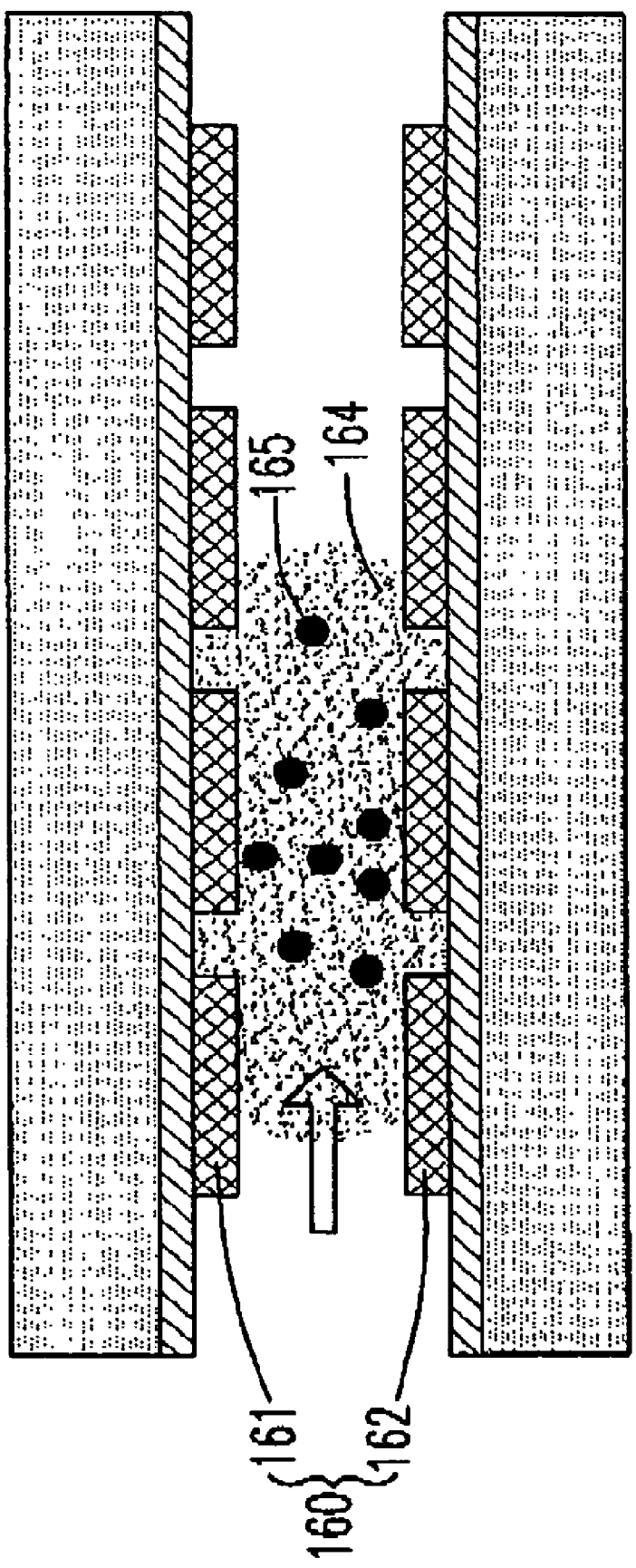
FIGS. 14(a) and 14(b) are diagrams illustrating the movement of the droplet in the detecting device according to the preferred embodiment of the present invention.
Figure 14B:
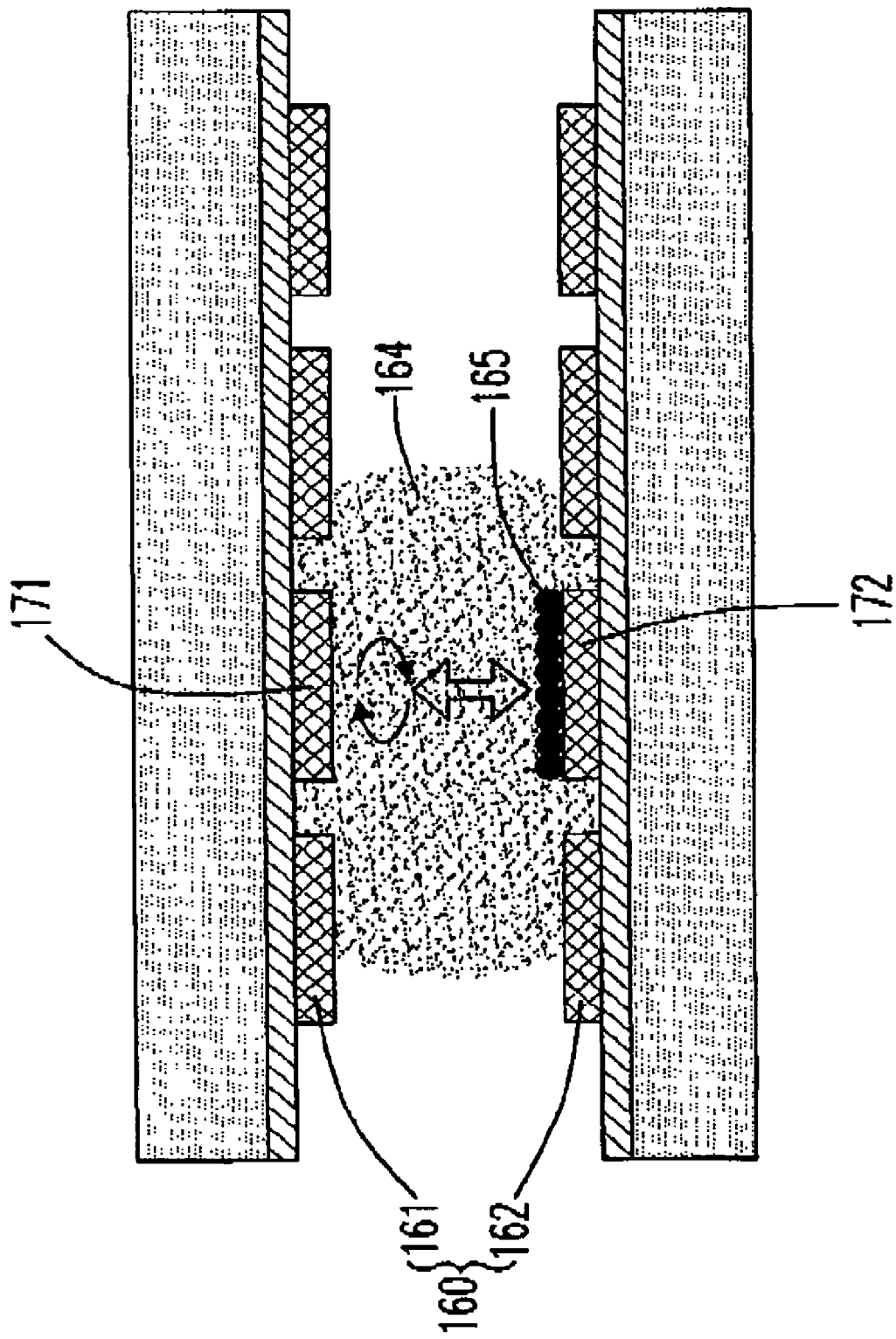

Please refer to FIGS. 14(a) and 14(b), which illustrate the different operation modes of the detecting device according to the present invention. By controlling the voltage and currents applied on the electrode, two operation modes of the droplets driving and the magnetic field inducing are able to be switched. The droplets 164 and the magnetic beads 165 are controlled by the electrode set 160 having the first electrode 161 and the second electrode 162 at the same time. In other words, the metal layer on the detecting zone of the detecting device is adjusted to be an electrode for driving the droplets and an electromagnet to attract the magnetic beads. As shown in FIG. 14(a), the second electrode 160 includes an upper sub-electrode 161 and a lower sub-electrode 162. While the upper sub-electrode 161 is connected to a high potential and the lower sub-electrode 162 is grounded, the droplet 164, which contains plural magnetic beads 165 therein, is driven to move forwardly. The droplet 164 is movable because the upper edge thereof is converted to a hydrophilic surface through the electrowetting function and the original shape of the droplet 164 is destructed for the change of the contact angle. Therefore, a pressure difference is generated inside the droplet 164 to push the droplet move. As shown in FIG. 14(b), the lower sub-electrode 172 is used as an electromagnet while the detecting is going to be initiated. The magnetic beads 165 are attracted on the zigzag-shaped electrode 172 when the current is applied thereon. An electric field is applied on the electrode 171, which is comb-shaped for making the cathode and the anode thereof interlace with each other, to initiate the oxidation-reduction reaction and detect the currents outside. The other electrodes are electrically disconnected while the detection operates. When the detection is finished, the zigzag-shaped electrode 172 is electrically disconnected, and the electric field applied on the electrode 171 is also removed and the magnet beads 165 will be redistributed in the droplet 164 for the magnetic field disappearing. The magnetic-bead redistribution occurs due that there is no residual magnetism inside the magnetic beads 165 when the magnetic field is removed owing to an intrinsic property of the magnetic beads.

The magnetic-bead detection is finished through the above operation, and the droplets are movable and taken away from the detecting device by controlling the electrodes. Multiple and various detections, such as carrying the reagent, adsorbing the magnetic beads, washing and removing the reagents, and detecting the reactions, are operated by the electrode controlling. A multiplex electrode is accordingly provided by the present invention, wherein an additional magnetic field inducer for the different positions of the magnetic beads is needless, and the detection is controlled more conveniently and precisely.

The electromagnet provided by the present invention is made through changing the electrode shape of the electrowetting device, and the electromagnet is hence simultaneously manufactured on the same chip with the whole electrowetting device. Complicated MEMS processes for fabricating the conventional detecting device, i.e. separately manufacturing the electromagnet and the microfludic channel on different chips and then assembling them in joint, are prevented therefore. The present invention provides a detecting device more practical than the conventional magnetic-beads detecting device to combine with other microfludic systems. Furthermore, since the detecting device is multiplex for the combination of the electrowetting driving electrodes and the electromagnets, an additional magnetic inducer or signal-detecting device is needless accordingly.

Hence, the present invention not only has a novelty and a progressiveness, but also has an industry utility.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A magnetic beads biochemical detecting device for detecting a target in a plurality of magnetic beads of a droplet, comprising:
    a first substrate;
    a magnetic layer located on said first substrate;
    an isolation layer located on said magnetic layer;
    at least a first electrode located on said isolation layer, wherein said first electrode is zigzag-shaped;
    a first dielectric layer located on said first electrode;
    a first hydrophobic layer located on said first dielectric layer;
    a second substrate;
    at least a second electrode located on said second substrate and having a cathode and an anode, wherein said cathode and said anode are comb-shaped and are interlaced with each other;
    a second dielectric layer located on said second electrode; and
    a second hydrophobic layer located on said second dielectric layer;
    wherein said first substrate and said second substrate are respectively configured to make said first electrode and said second electrode face to each other and to form a gap therebetween; said droplet is movable in said gap by a voltage difference produced between said first electrode and said second electrode; a magnetic force for attracting said plurality of magnetic beads is induced by applying currents only on said first electrode; and a positive-and-negative interlaced electric field is generated by applying currents on said cathode and said anode for initiating a certain reaction of said target to further generate a signal of current to be detected.

2. The detecting device according to claim 1, wherein said magnetic layer is magnetized by said magnetic force.

3. The detecting device according to claim 1, wherein a magnetic line of force of said magnetic force is closed by said magnetic layer so as to reduce a dissipation of said magnetic line of force and enhance said magnetic force.

4. The detecting device according to claim 1, wherein said reaction is an oxidation-reduction reaction.

5. The detecting device according to claim 1, wherein said first substrate is a silicon substrate.

6. The detecting device according to claim 1, wherein said first electrode is made of a metal.

7. The detecting device according to claim 1, wherein said magnetic layer is made of a permalloy.

8. The detecting device according to claim 1, wherein said second substrate is a glass substrate.

9. The detecting device according to claim 1, wherein said second electrode is made of a transparent and electrically conductive material.

10. The detecting device according to claim 1, wherein said signal of current is forwarded by said cathode and said anode for being detected.

* * * * *